US00PP11850P2

(12) United States Plant Patent
Noodelijk

(10) Patent No.: US PP11,850 P2
(45) Date of Patent: May 1, 2001

(54) CHRYSANTHEMUM PLANT NAMED 'ARES'

(75) Inventor: Robert Noodelijk, Woubrugge (NL)

(73) Assignee: Chrysanthemum Breeder Association N.V. (NL)

( * ) Notice: Subject to any disclaimer, the term of this patent is extended or adjusted under 35 U.S.C. 154(b) by 0 days.

(21) Appl. No.: 09/179,456

(22) Filed: Oct. 27, 1998

(51) Int. Cl.[7] ..... A01H 5/00
(52) U.S. Cl. ..... Plt./296
(58) Field of Search ..... Plt./286, 296

(56) References Cited

PUBLICATIONS

UPOV–ROM, Feb. 1999, Plant Variety Database, GTI Jouve Retrieval Software, citation for.*
UPOV–ROM, Feb. 1999, GTI Jouve Retrieval Software, two citations for 'Icarus'.*

* cited by examiner

*Primary Examiner*—Howard J. Locker
(74) *Attorney, Agent, or Firm*—Parkhurst & Wendel, L.L.P.

(57) ABSTRACT

A chrysanthemum plant named Helios characterized by its medium sized blooms with orange ray florets and yellow ray florets and prolific branching; early natural season flower date of August 4–7; blooming for a period of 5 weeks.

1 Drawing Sheet

BACKGROUND OF THE INVENTION

The new plant of the present invention comprises a new and distinct cultivar of chrysanthemum plant that is a cross of unknown *Dendranthema grandiflora* parents. The new and distinct cultivar was a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout, Holland in August, 1996. The plant has been asexually reproduced by cuttings in greenhouses at Rijsenhout, Holland. The new cultivar has been found to retain its distinctive characteristics through seccessive propagations.

SUMMARY OF THE INVENTION

The present invention is a new and distinct variety of chrysanthemum of a medium single bloom and orange color.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
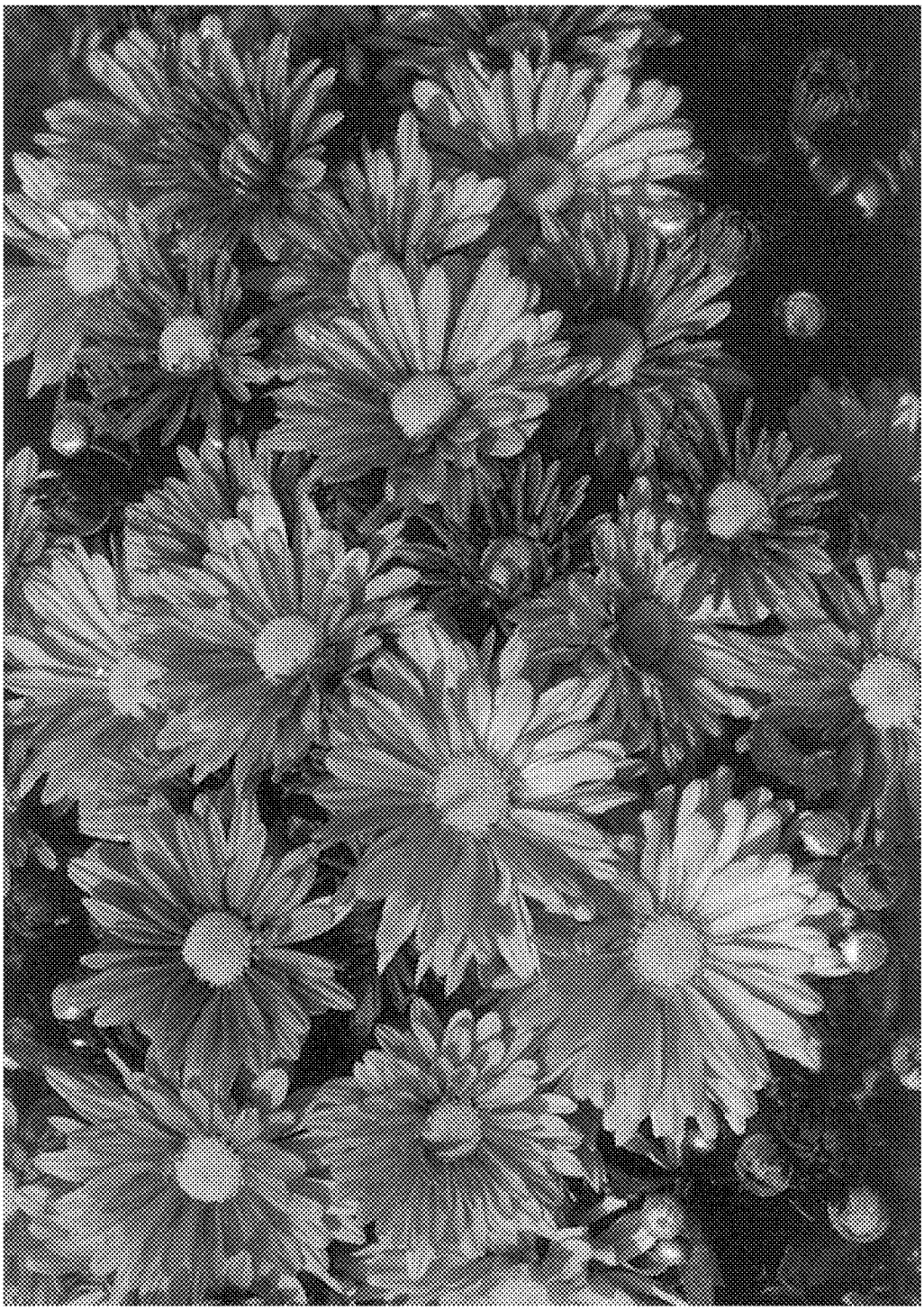
FIG. 1 shows the various stages of bloom of the new cultivar.

This new variety of chrysanthemum is of the botanical classification *Dendranthema grandiflora*. The observations and measurements were gathered from plants grown out doors in Rijsenhout, Holland under natural day length and temperature and planted week 22 in 1997 and 1998. The natural blooming date for this crop was August 4–7 (week 32). The average height of the plants was 22 cms. This new variety produces medium sized blooms with orange ray florets and yellow disc florets bloomimg for a period of 5 weeks. The photoperiodic response time is 45–47 days. The following is a description of the plant and characteristics that distinguish Ares as a new and distinct variety.

The color designations are taken from the plant itself. Accordingly, any discrepancies between the color designations (from the R.H.S Colour chart) and the colors depicted in the photographs are due to photographic tolerances.

Botanical classification:

*Bud size.*—Small cross section ±1.4 cm. Height ±1.5 cm.

*Outside color.*—Greyed-Orange 169A.

*Bloom size.*—Medium. Fully expanded: 6 cm. Borne (number of blooms per branch): Upper and lower portion plural blooms per branch (approx. 5 blooms). Length of lateral branch: From top to bottom approx. 12 cm. Lateral branch: Strong. Attachment branching: Prolific with 5–7 breaks after pinching. Form: Single (Daisy). Performance (on the plant): 5 weeks.

*Color.*—Center of flower: Yellow-Orange 16 A. Color of the upper surface of the majority of the ray-florets: Greyed-Orange 170B. Color of the lower surface of the majority of the ray-florets: Greyed-Red 178 B. Tonality from Distance: A compact gardenmum with medium size Greyed-Orange single blooms. Discoloration: To Greyed-Orange 168 D. Pollen: Yellow-Orange 14 A.

*Ray florets.*—Texture: Upperside smooth Underside smooth. Number: ±50–55. Cross-section: Flat. Longitudinal axis of the majority: Straight. Shape of tip: Round. Fragrance: Typical chrysanthemum.

*Disc Dismeter.*—Small, 1½ cm

*Reproductive Organs.*—Stamen: Yellow, thin ±5 mm in length. Pollen: Present, abundant. Styles: Yellow, thin. Style Length: ±5 mm. Stigmas: Yellow. Stigma width: ±2 mm. Ovaries: Enclosed in calyx.

*Plant.*—Form: A garden mum (pot mum) meant for outdoor use. Growth: Short. Height (from soil level): ±22 cm. Stem color: Near green 144 A. Stem strength: Strong. Stem brittleness: Present. Stem anthocyanin coloration: None. Natural blooming date: August 4–7 (week 32).

*Foliage.*—Color: Upperside green 137 A. Underside green 147 B. Size: Small: length ±8 cm. Width ±6 cm. Quantity (number per lateral branch): 10–14.

Shape: Lobed. Texture: Fleshy. Ribs and veins: Ribs and veins well developed. Edge: Lobed. Shape of base of sinus between lateral lobes: Round. Margin of sinus between lateral lobes: Diverging. Shape of base: Asymmetric. Apex: Mucronate.

I claim:

1. A new and distinct variety of chrysanthemum plant as described and illustrated.

* * * * *